US005948746A

United States Patent [19]

Sjøholm et al.

[11] Patent Number: 5,948,746

[45] Date of Patent: Sep. 7, 1999

[54] PROTEOLYTIC ENZYMES

[75] Inventors: Carsten Sjøholm, Allerød; Bjarne Rønfeldt Nielsen, Virum; Claus Dambmann, Søborg, all of Denmark

[73] Assignee: Novo Nordisk A/S, Bagsvæd, Denmark

[21] Appl. No.: 09/007,269

[22] Filed: Jan. 14, 1998

Related U.S. Application Data

[63] Continuation of application No. PCT/DK96/00299, Jul. 2, 1996.

[30] Foreign Application Priority Data

Jul. 19, 1995 [DK] Denmark .................................. 0844/95

[51] Int. Cl.[6] .............................. C11D 3/386; C12N 9/52

[52] U.S. Cl. .......................... 510/392; 510/530; 510/226; 510/320; 435/220; 435/872

[58] Field of Search .................................... 510/392, 530, 510/226, 320; 435/220, 872

[56] References Cited

U.S. PATENT DOCUMENTS 4,935,354 6/1990 Hayenga et al. ....................... 435/69.1
5,192,742 3/1993 Coates et al. ............................... 514/8

FOREIGN PATENT DOCUMENTS 0 653 490 5/1995 European Pat. Off. .
WO 94/00576 1/1994 WIPO .
97/04082 2/1997 WIPO .

OTHER PUBLICATIONS

Renko et al., S. rimosus extracellular proteases, pp. 39–44 (1989).

*Primary Examiner*—Kery Fries
*Attorney, Agent, or Firm*—Steve T. Zelson, Esq.; Elias J. Lambiris, Esq.

[57] ABSTRACT

The present invention relates to novel proteolytic enzymes. More specifically, the present invention relates to proteolytic enzymes obtainable from strains of Amycolata and Amycolatopsis. Moreover the invention relates to a process for the preparation of the proteolytic enzyme of the invention, as well as detergent additives and detergent compositions comprising the proteolytic enzyme.

23 Claims, 5 Drawing Sheets

PROTEOLYTIC ENZYMES

CROSS-REFERENCE TO RELATED APPLICATIONS

This application is a continuation application serial no. PCT/DK96/00299 filed Jul. 2, 1996 and claims priority under 35 U.S.C. 119 of Danish application serial no. 0844/95 filed Jul. 19, 1995, the contents of which are fully incorporated herein by reference.

FIELD OF THE INVENTION

The present invention relates to novel proteolytic enzymes. More specifically, the present invention relates to proteolytic enzymes obtainable from strains of Amycolata and Amycolatopsis. Moreover the invention relates to a process for the preparation of the proteolytic enzyme of the invention, as well as to its use in methods for making cheese and in detergent additives and detergent compositions.

BACKGROUND ART

Proteolytic enzymes find widespread commercial applications and have been successfully implemented in quite different industries such as the detergent, leather, chemical, agricultural, pharmaceutical, food and dairy industries.

In order to provide the industry with more alternatives to established enzymatic processes, and in order to offer an improved cost/performance ratio, extensive research in finding new enzymes takes place.

In 1986 two new genera of nocardioform actinomyces, termed Amycolata and Amycolatopsis, were described [Lechevalier M P, Prauser H, Labeda D P and Ruan J S; *Int. J. Sys. Bacteriol.* 1986 36 (1) 29–37]. However, proteolytic enzymes obtained from Amycolata or Amycolatopsis have never been isolated or characterized.

SUMMARY OF THE INVENTION

It is an object of the present invention to provide novel proteolytic enzymes useful in industrial applications. A particular object of the present invention is to provide a microbial alternative to trypsin.

Accordingly the present invention provides a novel proteolytic enzyme derived from a strain of Amycolata, or a strain of Amycolatopsis.

In another aspect, the invention provides a process for the preparation of the proteolytic enzyme of the invention, which process comprises cultivation of a protease producing strain of Amycolata or a protease producing strain of Amycolatopsis in a suitable nutrient medium, containing carbon and nitrogen sources and other inorganic salts, followed by recovery of the proteolytic enzyme.

In a third aspect, the invention provides a process for the preparation of the proteolytic enzyme of the invention, which process comprises isolating a DNA fragment encoding the proteolytic enzyme; combining the DNA fragment with an appropriate expression signal in an appropriate plasmid vector; introducing the plasmid vector into an appropriate host either as an autonomously replicating plasmid or integrated into the chromosome; cultivating the host organism under conditions leading to expression of the proteolytic enzyme; and recovering of the proteolytic enzyme from the culture medium.

In further aspects, the invention provides a process of making cheese, a detergent composition, as well as a detergent additive comprising the proteolytic enzyme of the invention.

BRIEF DESCRIPTION OF THE DRAWINGS

The present invention is further illustrated by reference to the accompanying drawing, in which.

DETAILED DISCLOSURE OF THE INVENTION

Figure 1:
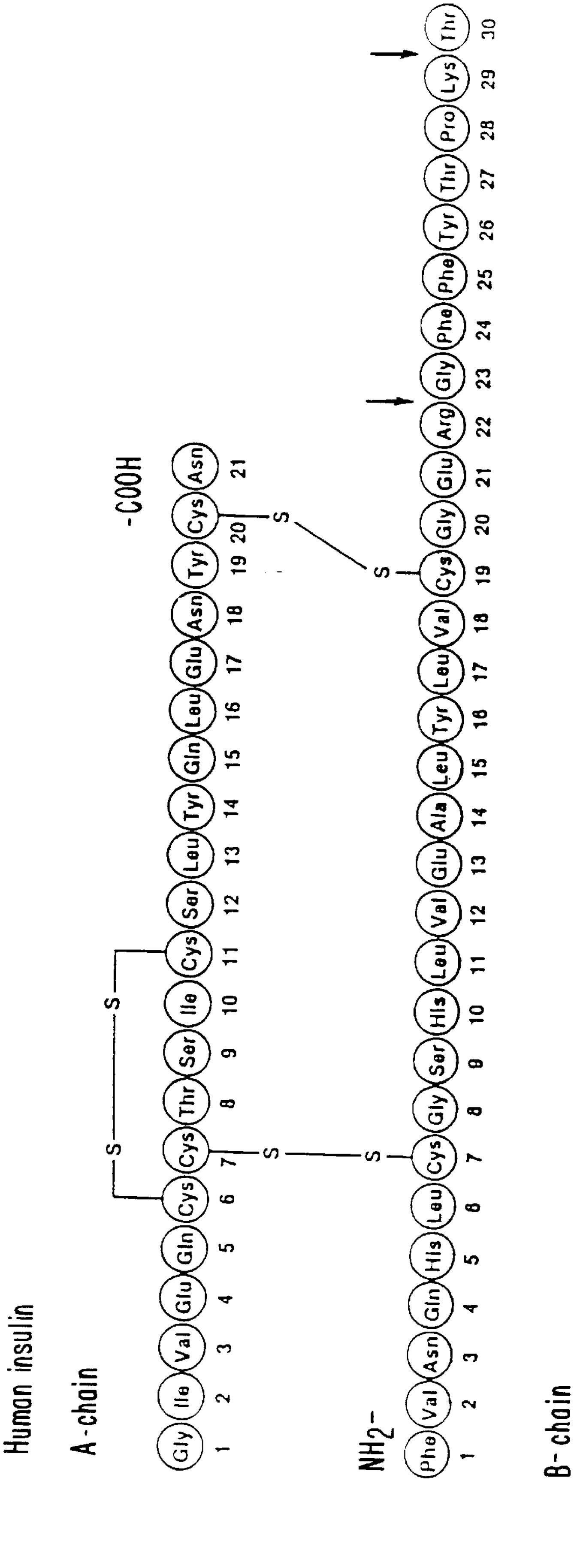
FIG. 1 shows the structure of human insulin, and the arrows indicates where insulin is cleaved by the enzyme of the invention.

The present invention provides a novel proteolytic enzyme derived from a strain of Amycolata or a strain of Amycolatopsis.

In the context of this invention, an enzyme derived from a strain of Amycolata or a strain of Amycolatopsis encompasses an enzyme naturally produced by such strains, either recovered from these strains or encoded by a DNA sequence isolated from such strains and produced in a host organism transformed with said DNA sequence. The enzyme of the invention may be characterized differently as an enzyme endogenous to a strain of Amycolata or a strain of Amycolatopsis. The term “endogenous to” is regarded as an art-defined term identifying the genomic source of the enzyme, no matter what organism, native or transformant, is used to produce the enzyme.

In a preferred embodiment, the proteolytic enzyme of the invention is one derived from a strain of Amycolatopsis. More preferred, the proteolytic enzyme is derived from a strain of *Amycolatopsis mediterranei*, a strain of *Amycolatopsis methanolica*, a strain of *Amycolatopsis fastidiosa*, a strain of *Amycolatopsis orientalis*, a strain of *Amycolatopsis rugosa*, or a strain of *Amycolatopsis sulphurea.*

Preferably, the proteolytic enzyme of the invention is derived from a strain of *Amycolatopsis mediterranei.* More preferred, the proteolytic enzyme is one derived from the strain *Amycolatopsis mediterranei* ATCC 13685, the strain *Amycolatopsis mediterranei* ATCC 21271, the strain *Amycolatopsis mediterranei* ATCC 21411, the strain *Amycolatopsis mediterranei* ATCC 21789, the strain *Amycolatopsis mediterranei* ATCC 27642, the strain *Amycolatopsis mediterranei* ATCC 31064, the strain *Amycolatopsis mediterranei* ATCC 31065, the strain *Amycolatopsis mediterranei* ATCC 31066, or mutants or variants thereof.

In its most preferred embodiment, the proteolytic enzyme of the invention is one derived from the strain *Amycolatopsis mediterranei* ATCC 13685, or a mutant or a variant thereof.

In another preferred embodiment, the proteolytic enzyme of the invention is one derived from a strain of Amycolata. More preferred, the proteolytic enzyme is derived from a strain of *Amycolata autotrophica*, a strain of *Amycolata hydrocarbonoxydans*, or a strain of *Amycolata saturnea.*

Physico-chemical Characteristics

In more specific embodiments, the proteolytic enzyme of the invention may be further characterized by one or more of the following physico-chemical characteristics.

The proteolytic enzyme is an endo-peptidase capable of cleaving lysyl and/or arginyl bonds of a peptide chain. This specific activity is characteristic for trypsin, and enzymes sharing this characteristic activity with trypsin are thus called trypsin-like enzymes. Trypsin-like proteases is a subgroup of proteolytic enzymes of particular interest to the industry. Trypsin is of animal origin, obtained by extraction of the pancreatic glands of slaughtered animals, usually pigs. Relatively few alternatives of microbiological origin exists. The present invention thus represents another microbial alternative to trypsin.

The proteolytic enzyme has activity from temperatures below 15° C. to above 70° C., and a temperature optimum within the range of from 30 to 45° C., around 40° C., when determined at pH 9.5 on casein as substrate.

The proteolytic enzyme has activity at pH values of from below 6 to above 11, with a pH optimum in the range of from about pH 7 to about pH 11, showing more than 90% activity in the range of from about pH 8 to about pH 11, when determined at 25° C. on casein as substrate.

The proteolytic enzyme has a molecular weight of about 33 kDa as determined by SDS-PAGE.

The proteolytic enzyme has an isoelectric point (pI) of about 9.1 as determined by isoelectric focusing on LKB Ampholine® PAG plates (pH 3.5–9.5).

The proteolytic enzyme shows strong activity towards the Z-Arg-pNA (ZAPA) substrate, but no activity on the Suc-Ala-Ala-Pro-Phe-pNA substrate.

The proteolytic enzyme is stable for 1 hour at 40° C. in standard liquid and powder detergent compositions.

Immuno-chemical Properties

The proteolytic enzyme of the invention has immunochemical properties identical or partially identical (i.e. at least partially identical) to those of a protease derived from the strain *Amycolatopsis mediterranei* ATCC 13685.

The immunochemical properties can be determined by immunological cross-reaction identity tests. The identity tests may e.g. be performed by the well-known Ouchterlony double immunodiffusion procedure, or by tandem crossed immunoelectrophoresis according to I. M. Roitt; *Immunology*, Gower Medical Publishing, 1985, or according to N. H. Axelsen; *Handbook of Immunoprecipitation-in-Gel Techniques*; Blackwell Scientific Publications, 1983, chapters 5 and 14. The terms "immunochemical identity" (antigenic identity) and "partial immunochemical identity" (partial antigenic identity) are described in Axelsen, supra, chapters 5, 19 and 20, and in Roitt, supra, chapter 6.

Monospecific antiserum for use in immunological tests can be raised, e.g. in rabbits, against the purified enzyme of the invention, e.g. as described in chapter 41 of Axelsen, supra, or chapter 23 of Axelsen et al., *A Manual of Quantitative Immunoelectrophoresis*, Blackwell Scientific Publications (1973).

Methods of Preparation

The proteolytic enzyme of the invention may be obtained by cultivation of a strain of Amycolata or a strain of Amycolatopsis.

Accordingly, in another aspect, the invention provides a process for the preparation of a proteolytic enzyme, which process comprises cultivation of a protease producing strain of Amycolata or a protease producing strain of Amycolatopsis in a suitable nutrient medium, containing carbon and nitrogen sources and other inorganic salts, followed by recovery of the proteolytic enzyme.

In a preferred embodiment, the protease producing strain is a strain of *Amycolatopsis mediterranei*, a strain of *Amycolatopsis methanolica*, a strain of *Amycolatopsis fastidiosa*, a strain of *Amycolatopsis orientalis*, a strain of *Amycolatopsis rugosa*, or a strain of *Amycolatopsis sulphurea*.

Preferably, the protease producing strain is a strain of *Amycolatopsis mediterranei*. More preferred, the protease producing strain is the strain *Amycolatopsis mediterranei* ATCC 13685, the strain *Amycolatopsis mediterranei* ATCC 21271, the strain *Amycolatopsis mediterranei* ATCC 21411, the strain *Amycolatopsis mediterranei* ATCC 21789, the strain *Amycolatopsis mediterranei* ATCC 27642, the strain *Amycolatopsis mediterranei* ATCC 31064, the strain *Amycolatopsis mediterranei* ATCC 31065, the strain *Amycolatopsis mediterranei* ATCC 31066, or a mutant or a variant thereof. Most preferred, the protease producing strain is strain *Amycolatopsis mediterranei* ATCC 13685, or a mutant or a variant thereof.

In another preferred embodiment, the protease producing strain is a strain of *Amycolata autotrophica*, a strain of *Amycolata hydrocarbonoxydans*, or a strain of *Amycolata saturnea*.

As defined herein, a mutant or a variant strain is a strain retaining the ability of the cited strain to produce the same respective proteolytic enzyme.

The protease producing strain may be cultivated under aerobic conditions in a nutrient medium containing assimilable carbon and nitrogen together with other essential nutrients, the medium being composed in accordance with the principles of the known art.

Suitable carbon sources are carbohydrates such as sucrose, glucose and starch, or carbohydrate containing materials such as soy bean grits, cotton seed flour, cereal grain, malt, rice and sorghum. The carbohydrate concentration incorporated in the medium may vary widely, e.g. up to 25% and down to 1–5%, but usually 8–10% will be suitable, the percentages being calculated as equivalents of glucose.

The nitrogen source in the nutrient medium may be of inorganic and/or organic nature. Suitable inorganic nitrogen sources are nitrates and ammonium salts. Among the organic nitrogen sources quite a number are used regularly in fermentation processes. Illustrative examples are soybean meal, cotton seed meal, peanut meal, casein, corn, corn steep liquor, yeast extract, urea and albumin. In addition, the nutrient medium should also contain usual trace substances.

After cultivation, the proteolytic enzyme may be recovered by conventional method for isolation and purification of polypeptides from a culture broth. Well-known purification procedures include separating the cells from the medium by centrifugation or filtration, precipitating proteinaceous components of the medium by means of a salt such as ammonium sulfate, and chromatographic methods such as e.g. ion exchange chromatography, gel filtration chromatography, affinity chromatography, etc.

However, the proteolytic enzyme of the invention may also, and more preferably, be obtainable by recombinant DNA technology by methods known in the art per se. In this respect reference is made to Sambrook et al.; *Molecular Cloning: A Laboratory Manual*; Cold Spring Harbor, N.Y., 1989. In general such methods comprises the steps of isolating a DNA fragment encoding the proteolytic enzyme; combining the DNA fragment with an appropriate expression signal in an appropriate plasmid vector; introducing the plasmid vector into an appropriate host, in particular a strain of *Escherichia coli*, a strain of Bacillus, a strain of Aspergillus, or a strain of Streptomyces, either as an autonomously replicating plasmid or integrated into the chromosome; cultivating the host organism under conditions leading to expression of the proteolytic enzyme; and recovering of the proteolytic enzyme from the culture medium.

Industrial Applications

The proteolytic enzyme of the invention may be useful in very different industrial applications. In particular the proteolytic enzyme of the invention may find use as a microbial alternative to trypsin, and as such it may primarily find its use in the food and dairy industries, in the detergent industry, in the leather industry, and in the pharmaceutical industry.

In a preferred embodiment, the proteolytic enzyme of the invention may be used in a process for making cheese, in which process the proteolytic enzyme is added to the milk portion, or any part of it, in the course of the process. In particular, in such a cheese making process, the enzyme of the invention may find use as rennet, as a cheese ripening enzyme, or as a combined rennet and cheese ripening enzyme.

From experiments it was found that when added to the milk in the course of the cheese making process, the proteolytic enzyme of the invention increased the amount of soluble nitrogen in the cheese, thereby accelerating the natural ripening of cheese without actually spoiling the cheese.

In another preferred embodiment, the proteolytic enzyme of the invention may be used in detergent compositions.

Detergent Compositions

The proteolytic enzyme of the invention may typically be a component of a detergent composition. As such, it may be included in the detergent composition in the form of a non-dusting granulate, a stabilized liquid, or a protected enzyme. Non-dusting granulates may be produced, e.g., as disclosed in U.S. Pat. No. 4,106,991 and 4,661,452 (both to Novo Industri A/S) and may optionally be coated by methods known in the art. Examples of waxy coating materials are poly(ethylene oxide) products (polyethyleneglycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g: as powder, granules, paste or liquid. A liquid detergent may be aqueous, typically containing up to 70% water and 0–30% organic solvent, or non-aqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as an amylase, a lipase, a cutinase, a protease, a cellulase, a peroxidase, and/or an oxidase, e.g. a laccase.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or or alkenylsuccinic acid, soluble silicates or layered silicates (e.g. SKS-6 from Hoechst). The detergent may also be un-built, i.e. essentially free of detergent builder.

The detergent may comprise one or more polymers. Examples are carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of, e.g., the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil-redeposition agents, dyes, bactericides, optical brighteners, or perfume.

The pH (measured in aqueous solution at use concentration) will usually be neutral or alkaline, e.g. in the range of 7–11.

Particular forms of detergent compositions within the scope of the invention include:

1) A detergent composition formulated as a granulate having a bulk density of at least 600 g/l comprising

| | |
|---|---|
| Linear alkylbenzenesulfonate (calculated as acid) | 7–12% |
| Alcohol ethoxysulfate (e.g., $C_{12-18}$ alcohol, 1–2 EO) or alkyl sulfate (e.g., $C_{16-18}$) | 1–4% |
| Alcohol ethoxylate (e.g., $C_{14-15}$ alcohol, 7 EO) | 5–9% |
| Sodium carbonate (as $Na_2CO_3$) | 14–20% |
| Soluble silicate (as $Na_2O$, $2SiO_2$) | 2–6% |
| Zeolite (as $NaA1SiO_4$) | 15–22% |
| Sodium sulfate (as $Na_2SO_4$) | 0–6% |
| Sodium citrate/citric acid (as $C_6H_5Na_3O_7/C_6H_8O_7$) | 0–15% |
| Sodium perborate (as $NaBO_3.H_2O$) | 11–18% |
| TAED | 2–6% |
| Carboxymethylcellulose | 0–2% |
| Polymers (e.g., maleic/acrylic acid copolymer, PVP, PEG) | 0–3% |
| Enzymes (calculated as pure enzyme protein) | 0.0001–0.1% |
| Minor ingredients (e.g., suds suppressors, perfume, optical brightener, photobleach) | 0–5% |

2) A detergent composition formulated as a granulate having a bulk density of at least 600 g/l comprising

| | |
|---|---|
| Linear alkylbenzenesulfonate (calculated as acid) | 6–11% |
| Alcohol ethoxysulfate (e.g., $C_{12-18}$ alcohol, 1–2 EO or alkyl sulfate (e.g., $C_{16-18}$) | 1–3% |
| Alcohol ethoxylate (e.g., $C_{14-15}$ alcohol, 7 EO) | 5–9% |
| Sodium carbonate (as $Na_2CO_3$) | 15–21% |
| Soluble silicate (as $Na_2O$, $2SiO_2$) | 1–4% |
| Zeolite (as $NaA1SiO_4$) | 24–34% |

-continued

| | |
|---|---|
| Sodium sulfate (as $Na_2SO_4$) | 4–10% |
| Sodium citrate/citric acid (as $C_6H_5Na_3O_7/C_6H_8O_7$) | 0–15% |
| Carboxymethylcellulose | 0–2% |
| Polymers (e.g., maleic/acrylic acid copolymer, PVP, PEG) | 1–6% |
| Enzymes (calculated as pure enzyme protein) | 0.0001–0.1% |
| Minor ingredients (e.g., suds suppressors, perfume) | 0–5% |

3) A detergent composition formulated as a granulate having a bulk density of at least 600 g/l comprising

| | |
|---|---|
| Linear alkylbenzenesulfonate (calculated as acid) | 5–9% |
| Alcohol ethoxylate (e.g., $C_{12-15}$ alcohol, 7 EO) | 7–14% |
| Soap as fatty acid (e.g., $C_{16-22}$ fatty acid) | 1–3% |
| Sodium carbonate (as $Na_2CO_3$) | 10–17% |
| Soluble silicate (as $Na_2O$, $2SiO_2$) | 3–9% |
| Zeolite (as $NaA1SiO_4$) | 23–33% |
| Sodium sulfate (as $Na_2SO_4$) | 0–4% |
| Sodium perborate (as $NaBO_3.H_2O$) | 8–16% |
| TAED | 2–8% |
| Phosphonate (e.g., EDTMPA) | 0–1% |
| Carboxymethylcellulose | 0–2% |
| Polymers (e.g., maleic/acrylic acid copolymer, PVP, PEG) | 0–3% |
| Enzymes (calculated as pure enzyme protein) | 0.0001–0.1% |
| Minor ingredients (e.g., suds suppressors, perfume, optical brightener) | 0–5% |

4) A detergent composition formulated as a granulate having a bulk density of at least 600 g/l comprising

| | |
|---|---|
| Linear alkylbenzenesulfonate (calculated as acid) | 8–12% |
| Alcohol ethoxylate (e.g., $C_{12-15}$ alcohol, 7 EO) | 10–25% |
| Sodium carbonate (as $Na_2CO_3$) | 14–22% |
| Soluble silicate (as $Na_2O$, $2SiO_2$) | 1–5% |
| Zeolite (as $NaA1SiO_4$) | 25–35% |
| Sodium sulfate (as $Na_2SO_4$) | 0–10% |
| Carboxymethylcellulose | 0–2% |
| Polymers (e.g., maleic/acrylic acid copolymer, PVP, PEG) | 1–3% |
| Enzymes (calculated as pure enzyme protein) | 0.0001–0.1% |
| Minor ingredients (e.g., suds suppressors, perfume) | 0–5% |

5) An aqueous liquid detergent composition comprising

| | |
|---|---|
| Linear alkylbenzenesulfonate (calculated as acid) | 15–21% |
| Alcohol ethoxylate (e.g., $C_{12-15}$ alcohol, 7 EO or $C_{12-15}$ alcohol, 5 EO) | 12–18% |
| Soap as fatty acid (e.g., oleic acid) | 3–13% |
| Alkenylsuccinic acid ($C_{12-14}$) | 0–13% |
| Aminoethanol | 8–18% |
| Citric acid | 2–8% |
| Phosphonate | 0–3% |
| Polymers (e.g., PVP, PEG) | 0–3% |
| Borate (as $B_4O_7$) | 0–2% |
| Ethanol | 0–3% |
| Propylene glycol | 8–14% |
| Enzymes (calculated as pure enzyme protein) | 0.0001–0.1% |
| Minor ingredients (e.g., dispersants, suds suppressors, perfume, optical brightener) | 0–5% |

6) An aqueous structured liquid detergent composition comprising

| | |
|---|---|
| Linear alkylbenzenesulfonate (calculated as acid) | 15–21% |
| Alcohol ethoxylate (e.g., $C_{12-15}$ alcohol, 7 EO, or $C_{12-15}$alcohol, 5 EO) | 3–9% |
| Soap as fatty acid (e.g., oleic acid) | 3–10% |
| Zeolite (as $NaA1SiO_4$) | 14–22% |
| Potassium citrate | 9–18% |
| Borate (as $B_4O_7$) | 0–2% |

-continued

| | |
|---|---|
| Carboxymethylcellulose | 0–2% |
| Polymers (e.g., PEG, PVP) | 0–3% |
| Anchoring polymers such as, e.g., lauryl methacrylate/acrylic acid copolymer; molar ratio 25:1; MW 3800 | 0–3% |
| Glycerol | 0–5% |
| Enzymes (calculated as pure enzyme protein) | 0.0001–0.1% |
| Minor ingredients (e.g., dispersants, suds suppressors, perfume, optical brighteners) | 0–5% |

7) A detergent composition formulated as a granulate having a bulk density of at least 600 g/l comprising

| | |
|---|---|
| Fatty alcohol sulfate | 5–10% |
| Ethoxylated fatty acid monoethanolamide | 3–9% |
| Soap as fatty acid | 0–3% |
| Sodium carbonate (as $Na_2CO_3$) | 5–10% |
| Soluble silicate (as $Na_2O$, $2SiO_2$) | 1–4% |
| Zeolite (as $NaA1SiO_4$) | 20–40% |
| Sodium sulfate (as $Na_2SO_4$) | 2–8% |
| Sodium perborate (as $NaBO_3.H_2O$) | 12–18% |
| TAED | 2–7% |
| Polymers (e.g., maleic/acrylic acid copolymer, PEG) | 1–5% |
| Enzymes (calculated as pure enzyme protein) | 0.0001–0.1% |
| Minor ingredients (e.g., optical brightener, suds suppressors, perfume) | 0–5% |

8) A detergent composition formulated as a granulate comprising

| | |
|---|---|
| Linear alkylbenzenesulfonate (calculated as acid) | 8–14% |
| Ethoxylated fatty acid monoethanolamide | 5–11% |
| Soap as fatty acid | 0–3% |
| Sodium carbonate (as $Na_2CO_3$) | 4–10% |
| Soluble silicate (as $Na_2O$, $2SiO_2$) | 1–4% |
| Zeolite (as $NaA1SiO_4$) | 30–50% |
| Sodium sulfate (as $Na_2SO_4$) | 3–11% |
| Sodium citrate (as $C_6H_5Na_3O_7$) | 5–12% |
| Polymers (e.g., PVP, maleic/acrylic acid copolymer, PEG) | 1–5% |
| Enzymes (calculated as pure enzyme protein) | 0.0001–0.1% |
| Minor ingredients (e.g., suds suppressors, perfume) | 0–5% |

9) A detergent composition formulated as a granulate comprising

| | |
|---|---|
| Linear alkylbenzenesulfonate (calculated as acid) | 6–12% |
| Nonionic surfactant | 1–4% |
| Soap as fatty acid | 2–6% |
| Sodium carbonate (as $Na_2CO_3$) | 14–22% |
| Zeolite (as $NaA1SiO_4$) | 18–32% |
| Sodium sulfate (as $Na_2SO_4$) | 5–20% |
| Sodium citrate (as $C_6H_5Na_3O_7$) | 3–8% |
| Sodium perborate (as $NaBO_3.H_2O$) | 4–9% |
| Bleach activator (e.g., NOBS or TAED) | 1–5% |
| Carboxymethylcellulose | 0–2% |
| Polymers (e.g., polycarboxylate or PEG) | 1–5% |
| Enzymes (calculated as pure enzyme protein) | 0.0001–0.1% |
| Minor ingredients (e.g., optical brightener, perfume) | 0–5% |

10) An aqueous liquid detergent composition comprising

| | |
|---|---|
| Linear alkylbenzenesulfonate (calculated as acid) | 15–23% |
| Alcohol ethoxysulfate (e.g., $C_{12-15}$ alcohol, 2–3 EO) | 8–15% |
| Alcohol ethoxylate (e.g., $C_{12-15}$ alcohol, 7 EO, or $C_{12-15}$alcohol, 5 EO) | 3–9% |
| Soap as fatty acid (e.g., lauric acid) | 0–3% |
| Aminoethanol | 1–5% |
| Sodium citrate | 5–10% |

-continued

| | |
|---|---|
| Hydrotrope (e.g., sodium toluensulfonate) | 2–6% |
| Borate (as $B_4O_7$) | 0–2% |
| Carboxymethylcellulose | 0–1% |
| Ethanol | 1–3% |
| Propylene glycol | 2–5% |
| Enzymes (calculated as pure enzyme protein) | 0.0001–0.1% |
| Minor ingredients (e.g., polymers, dispersants, perfume, optical brighteners) | 0–5% |

11) An aqueous liquid detergent composition comprising

| | |
|---|---|
| Linear alkylbenzenesulfonate (calculated as acid) | 20–32% |
| Alcohol ethoxylate (e.g., $C_{12-15}$ alcohol, 7 EO, or $C_{12-15}$ alcohol, 5 EO) | 6–12% |
| Aminoethanol | 2–6% |
| Citric acid | 8–14% |
| Borate (as $B_4O_7$) | 1–3% |
| Polymer (e.g., maleic/acrylic acid copolymer, anchoring polymer such as, e.g., lauryl methacrylate/acrylic acid copolymer) | 0–3% |
| Glycerol | 3–8% |
| Enzymes (calculated as pure enzyme protein) | 0.0001–0.1% |
| Minor ingredients (e.g., hydrotropes, dispersants, perfume, optical brighteners) | 0–5% |

12) A detergent composition formulated as a granulate having a bulk density of at least 600 g/l comprising

| | |
|---|---|
| Anionic surfactant (linear alkylbenzenesulfonate, alkyl sulfate, alpha-olefinsulfonate, alpha-sulfo fatty acid methyl esters, alkanesulfonates, soap) | 25–40% |
| Nonionic surfactant (e.g., alcohol ethoxylate) | 1–10% |
| Sodium carbonate (as $Na_2CO_3$) | 8–25% |
| Soluble silicates (as $Na_2O$, $2SiO_2$) | 5–15% |
| Sodium sulfate (as $Na_2SO_4$) | 0–5% |
| Zeolite (as $NaA1SiO_4$) | 15–28% |
| Sodium perborate (as $NaBO_3.4H_2O$) | 0–20% |
| Bleach activator (TAED or NOBS) | 0–5% |
| Enzymes (calculated as pure enzyme protein) | 0.0001–0.1% |
| Minor ingredients (e.g., perfume, optical brighteners) | 0–3% |

13) Detergent compositions as described in compositions 1–12 wherein all or part of the linear alkylbenzenesulfonate is replaced by ($C_{12}$–$C_{18}$) alkyl sulfate.

14) A detergent composition formulated as a granulate having a bulk density of at least 600 g/l comprising

| | |
|---|---|
| ($C_{12}$–$C_{18}$) alkyl sulfate | 9–15% |
| Alcohol ethoxylate | 3–6% |
| Polyhydroxy alkyl fatty acid amide | 1–5% |
| Zeolite (as $NaA1SiO_4$) | 10–20% |
| Layered disilicate (e.g., SK56 from Hoechst) | 10–20% |
| Sodium carbonate (as $Na_2CO_3$) | 3–12% |
| Soluble silicate (as $Na_2O$, $2SiO_2$) | 0–6% |
| Sodium citrate | 4–8% |
| Sodium percarbonate | 13–22% |
| TAED | 3–8% |
| Polymers (e.g., polycarboxylates and PVP) | 0–5% |
| Enzymes (calculated as pure enzyme protein) | 0.0001–0.1% |
| Minor ingredients (e.g., optical brightener, photo bleach, perfume, suds suppressors) | 0–5% |

15) A detergent composition formulated as a granulate having a bulk density of at least 600 g/l comprising

| | |
|---|---|
| ($C_{12}$–$C_{18}$) alkyl sulfate | 4–8% |
| Alcohol ethoxylate | 11–15% |

-continued

| | |
|---|---|
| Soap | 1–4% |
| Zeolite MAP or zeolite A | 35–45% |
| Sodium carbonate (as $Na_2CO_3$) | 2–8% |
| Soluble silicate (as $Na_2O$, $2SiO_2$) | 0–4% |
| Sodium percarbonate | 13–22% |
| TAED | 1–8% |
| Carboxymethyl cellulose | 0–3% |
| Polymers (e.g., polycarboxylates and PVP) | 0–3% |
| Enzymes (calculated as pure enzyme protein) | 0.0001–0.1% |
| Minor ingredients (e.g., optical brightener, phosphonate, perfume) | 0–3% |

16) Detergent compositions as described in compositions 1–15 which contain a stabilized or encapsulated peracid, either as an additional component or as a substitute for already specified bleach systems.

17) Detergent compositions as described in 1), 3), 7), 9) and 12) wherein perborate is replaced by percarbonate.

18) Detergent compositions as described in 1), 3), 7), 9), 12), 14) and 15) which additionally contain a manganese catalyst. The manganese catalyst may, e.g., be one of the compounds described in "Efficient manganese catalysts for low-temperature bleaching", *Nature* 369, 1994, pp. 637–639.

19) Detergent composition formulated as a nonaqueous detergent liquid comprising a liquid nonionic surfactant such as, e.g., linear alkoxylated primary alcohol, a builder system (e.g. phosphate), enzyme and alkali. The detergent may also comprise anionic surfactant and/or a bleach system.

The proteolytic enzyme of the invention may be incorporated in concentrations conventionally employed in detergents. It is at present contemplated that, in the detergent composition of the invention, the proteolytic enzyme of the invention may be added in an amount corresponding to 0.00001–1 mg (calculated as pure enzyme protein) of proteolytic enzyme per liter of wash liquor.

EXAMPLES

The invention is further illustrated with reference to the following examples which are not intended to be in any way limiting to the scope of the invention as claimed.

Example 1

Cultivation Example

The strain, Amycolatopsis mediterranei ATCC 13685, was cultivated in a medium of the following composition:

| | |
|---|---|
| Soy meal | 20 g/l |
| $Na_2HPO_4$, 12 $H_2O$ | 10 g/l |
| $K_2HPO_4$ | 2 g/l |
| Pluronic ™ | 3 g/l |
| Sucrose | 30 g/l |
| pH adjusted to 6.7 | |

After 7 days of cultivation at 30° C., the supernatant was separated by centrifugation.

Example 2

Purification Example

The supernatant obtained according to Example 1 was subjected to standard purification techniques including precipitation with ammonium sulfate, followed by separation by anion exchange and cation exchange chromatography.

Ammonium sulfate precipitation (80% saturation) was carried out under stirring for 30 minutes at ambient temperature. The precipitate was separated, re-suspended, and filtered through a 0.45 mm filter. The solution was subjected to dialysis against a buffer containing 50 mM boric acid, 10 mM 3,3-dimnethylglutaric acid (DMG), 2 mM $CaCl_2$, pH 6.5 (Buffer A).

Anion exchange chromatography was carried out at pH 7.5 using DEAE Sephadex™ A50 (Pharmacia). Proteolytic activity present in the effluent was obtained and subjected to cation exchange chromatography. The sample was adjusted to pH 6 and then applied at 5 ml/minute to a 2.6 cm (i.d.)×10 cm S Sepharose™ HP column (Pharmacia) that had been equilibrated in Buffer A, above. The column was washed with 5 bed volumes of Buffer A, and the protease was eluted using a linear gradient from 0–0.3 M NaCl in Buffer A over 10 bed volumes.

5 ml fractions were collected and assayed for trypsin-like protease activity. 10 ml protease solution was added to 190 ml Benz-Arg-pNA (ZAPA) substrate in 100 mM TRIS-HCl, pH 9. The increase in absorbance at 405 nm was measured at ambient temperature for a 3 minutes period.

Example 3

Enzyme Characterization

Assay for Proteolytic Activity

The proteolytic activity may be determined using casein as substrate.

One Casein Protease Unit (CPU) is defined as the amount of enzyme liberating 1 mM of primary amino groups (determined by comparison with a serine standard) per minute under standard conditions, i.e. incubation for 30 minutes at 25° C. and pH 9.5.

A folder AF 228/1 describing this analytical method in more detail is available upon request to Novo Nordisk A/S, Denmark, which folder is hereby included by reference.

Temperature and pH Dependent Activities

The temperature activity relationship was determined with casein as substrate. The assay for proteolytic activity described above was used with the modification that the incubation temperature was varied in the interval of from 15 to 70° C. The result is shown in Table 1.

The enzyme possesses proteolytic activity from temperatures below 15° C. to above 70° C., and a temperature optimum within the range of from 30 to 45° C.; around 40° C. (determined at pH 9.5).

TABLE 1

Temperature Dependent Activity

| Temperature (° C.) | Activity (CPU) |
|---|---|
| 15 | 9 |
| 30 | 45 |
| 40 | 100 |
| 50 | 7 |
| 60 | 2 |
| 70 | 3 |

The dependence of activity on pH was determined by the same procedure, using buffers adjusted to predetermined pH values in the pH range of from 6 to 11. The result is shown in Table 2.

The enzyme possesses proteolytic activity at pH values below 6 to above 11, with a pH optimum in the range of from pH 7 to pH 11, showing more than 90% activity in the range of from about pH 8 to about pH 11 (determined at 25° C.).

TABLE 2 pH Dependent Activity

| pH | Activity (CPU) |
|---|---|
| 6 | 43 |
| 7 | 82 |
| 8 | 100 |
| 9 | 95 |
| 10 | 91 |
| 11 | 99 |

SDS-PAGE

Sodium dodecylsulfate-polyacrylamide gel electrophoresis (SDS-PAGE) was accomplished using a 4–25% gradient gel from Novex. The gel was stained with Coomassie Blue. Standard molecular mass markers were from Pharmacia. A molecular weight (MW) of about 33 kDa was measured.

Isoelectric Point

Isoelectric focusing on LKB Ampholine® PAG plates (pH 3.5–9.5), followed by applying an overlayer-gel of agarose containing 1% skim milk at pH 9.3 over the isoelectric focusing gel and incubation for an appropriate time, showed a clearing zone around pH 9.3.

Substrate Specificity

The clearing zone obtained by isoelectric focusing described above showed strong activity on the Z-Arg-pNA (ZAPA) substrate, but no activity on the Suc-Ala-Ala-Pro-Phe-pNA substrate.

Detergent Stability 10 ml of the supernatant obtained according to Example 1 was applied to nitrocellulose papers (Schleicher & Schüell BA 85). The nitrocellulose papers were incubated for 1 hour in two American standard detergents (a standard liquid detergent and a standard powder detergent) at 40° C., and in a control borate buffer solution at 20° C., respectively.

Proteolytic activity is visualized by applying the nitrocellulose papers onto skim milkagarose plates, followed by incubation overnight at ambient temperature. By comparing the clearing zones of the detergent exposed proteases with the clearing zone of the control preparation, the detergent stability was evaluated.

The proteolytic enzyme of the invention showed essentially no activity decrease when exposed to the detergents.

Example 4

Trypsin-like Activity

It is known that proteases with specificity for the same amino acids do not necessarily hydrolyze proteins or peptides in the same way, cf. e.g. trypsin and plasmin, both specific for lysine and arginine bonds. The proteolytic enzyme of the invention has shown specificity for lysine and arginine when tested on small pNA-peptides. As the activity against the pNA-peptide is an exo-activity and the C—N bond to be hydrolyzed is not a peptide bond, it was obvious to look at the hydrolysis of a more protein-like substrate.

Human insulin was chosen for this purpose. Despite its size, human insulin resembles a protein in that it has a folded structure with sulfur-bridges. It was, however, also decided to look at the hydrolysis of peptide bonds in the less structured polypeptide, glucagon.

In this example, the activity of the proteolytic enzyme of the invention (designated Protease A, obtained according to examples 1–2) was compared to that of porcine trypsin (available from Novo Nordisk A/S, Denmark). The degradation products were separated by reverse-phase HPLC. The chromatograms showed clear differences between the action of the different proteases. It was therefore decided to follow the time course of the degradation, to determine the order of preference for each protease. The isolated fragments from glucagon were analyzed for N-terminal amino acids, thereby enabling exact determination of the hydrolyzed peptide bond.

pNA-peptides

Small peptides (3–4 amino acids) were coupled with para-nitroanilide (pNA) at the C-terminal. When hydrolyzed, the pNA group is liberated, causing a yellow color that can be measured spectrophotometrically at 405 nm.

The reaction conditions were 30° C., pH 9.5 using a 0.05 M borate/KCl buffer, and the substrate concentration was 2.5 mM pNA-peptide.

The change over time in absorbance at 405 nm was measured with an automatic system, <Cobas> FARA, and one unit of activity (1 U) is defined as the amount of enzyme capable of hydrolyzing 1 mM pNA-peptide per minute.

The following pNA-peptides were used:

N-suc-Ala-Ala-Pro-Phe-pNA (AAPF; Sigma S-7388)

MeO-suc-Ala-Ala-Pro-Met-pNA (AAPM; Protogen 03-32-0048)

N-suc-Ala-Ala-Pro-Leu-pNA (AAPL; Sigma S-3513)

N-tos-Gly-Pro-Lys-pNA (GPK; Sigma T-6140)

N-tos-Gly-Pro-Arg-pNA (GPR; Sigma T-1637)

Insulin and Glucagon Hydrolysates

Figure 2:
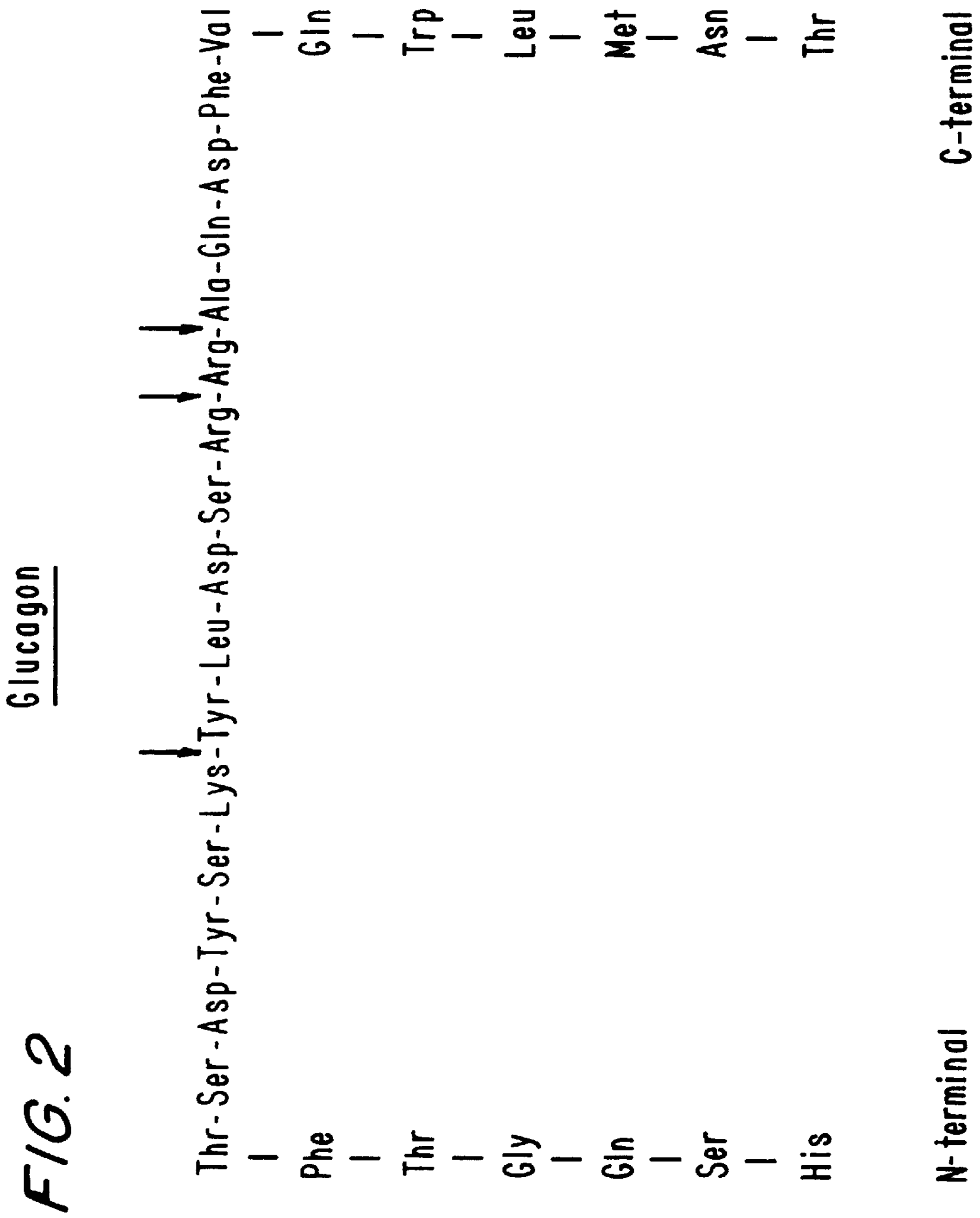
FIG. 2 shows the structure of glucagon, and the arrows indicates where insulin is cleaved by the enzyme of the invention.

The substrates were human insulin (FIG. 1, available from Novo Nordisk A/S, Denmark) and Glucagon (FIG. 2, available from Novo Nordisk A/S, Denmark), respectively, dissolved in Britton & Robinson Buffer, pH 9.5. The temperature was 37° C., and the reaction time 15, 30, 60 and 120 minutes, respectively. The enzyme concentration was 1 CPU/1, which CPU unit has been defined in the assay for proteolytic activity described in Example 3 above.

To 1 ml of substrate 0.150 ml enzyme solution was added. After incubation for the desired period of time, the reaction was terminated by adding 0.100 ml 1 M HCl. The reaction mixture was filtered through a 0.45 mm filter (Sartorius, Germany), and was ready for HPLC analysis.

HPLC Analysis

The HPLC system was from Shimadzu: 2 LC-8A pumps, SCL-6B controller unit, SPD-6AV detector, C-R4A integrator and SIL-6B auto-injector. The column was placed in a thermostated water bath.

The column was Hibar LiChrosorb RP-18, 5 m particles, 25 cm (Merck). Solvent A was 0.2 M sodium sulfate, 0.2 M phosphoric acid, pH 2.5, and solvent B was 50% acetonitrile (HPLC grade) in water. The solvents were made from Milli-Q-water, filtered through 0.45 mm filters and degassed.

The column was eluted and equilibrated in 60 minutes, using a 0–5 minutes linear gradient from 10% B to 20% B, a 5–45 minutes linear gradient from 20% B to 80% B, a 45–46 minutes linear gradient from 80% B to 10% B, and a 46–60 minutes equilibration.

The injection volume was 50 l, detection was carried out at 214 nm and the column temperature was 40° C.

The peaks were controlled either manually or with a Gibson Model 201 fraction collector.

Results

Hydrolysis of pNA-peptides

The results of the pNA-peptide hydrolysis is shown in Table 3, below.

TABLE 3

| pNA-peptide Hydrolysis | | | | | | |
|---|---|---|---|---|---|---|
| | Dosage | U/ml | | | | |
| Enzyme | CPU/ml | AAPF | AAPM | AAPL | GPK | GPR |
| Trypsin | 0.022 | 0 | 0 | 0 | 87 | 339 |
| Protease A | 0.027 | 0 | 0 | 0 | 455 | 2010 |

It appears from Table 3 that both proteases are specific for lysine and arginine, while the peptides with a hydrophobic amino acid as the C-terminal have not been hydrolyzed. Also, with this kind of substrates, arginine is the preferred amino acid.

Hydrolysis of Insulin

Figure 3A:
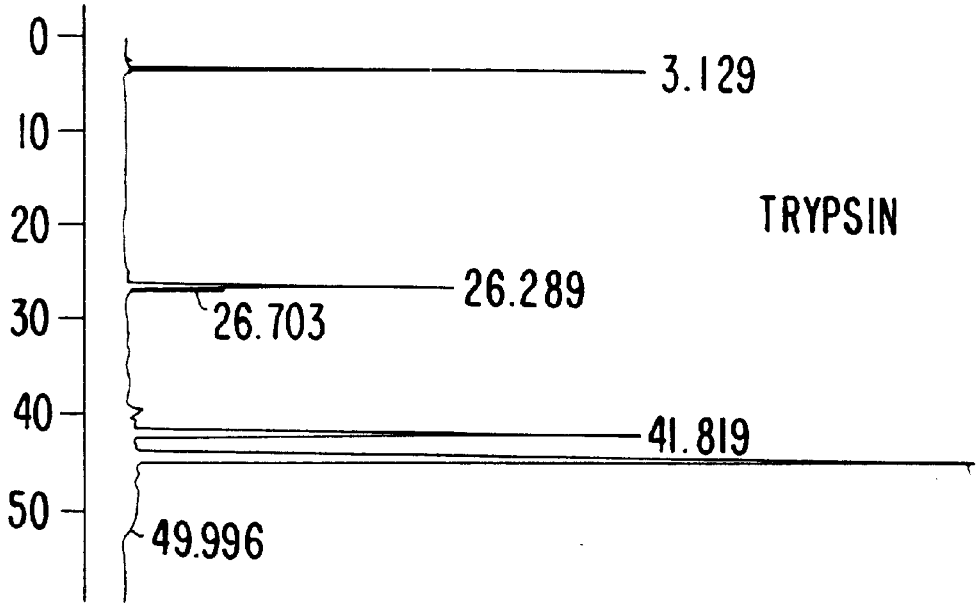
FIG. 3 shows the chromatograms obtained when human insulin is subjected to the action of trypsin (FIG. 3A), and an enzyme of the invention (ProtA, FIG. 3B), respectively (as obtained after 120 minutes of incubation)
Figure 3B:
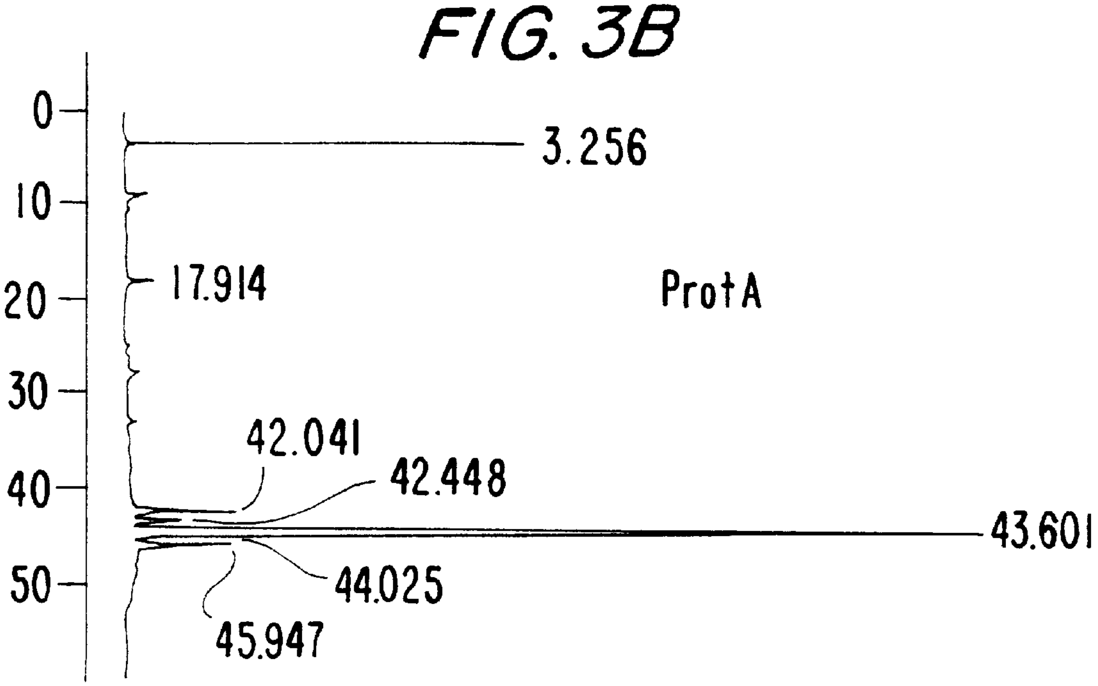

The results of the insulin hydrolysis are presented in FIG. 3. The chromatograms obtained with trypsin (FIG. 3A) shows two peaks (1 and 2) corresponding to the hydrolysis of the $Lys_{29}$-$Thr_{30}$ bond as the first choice, and the $Arg_{22}$-$Gly_{23}$ bond as the second choice. From the chromatogram obtained with the enzyme of the invention (ProtA, FIG. 3B) it appears that insulin is a poor substrate.

Hydrolysis of Glucagon

Figure 4:
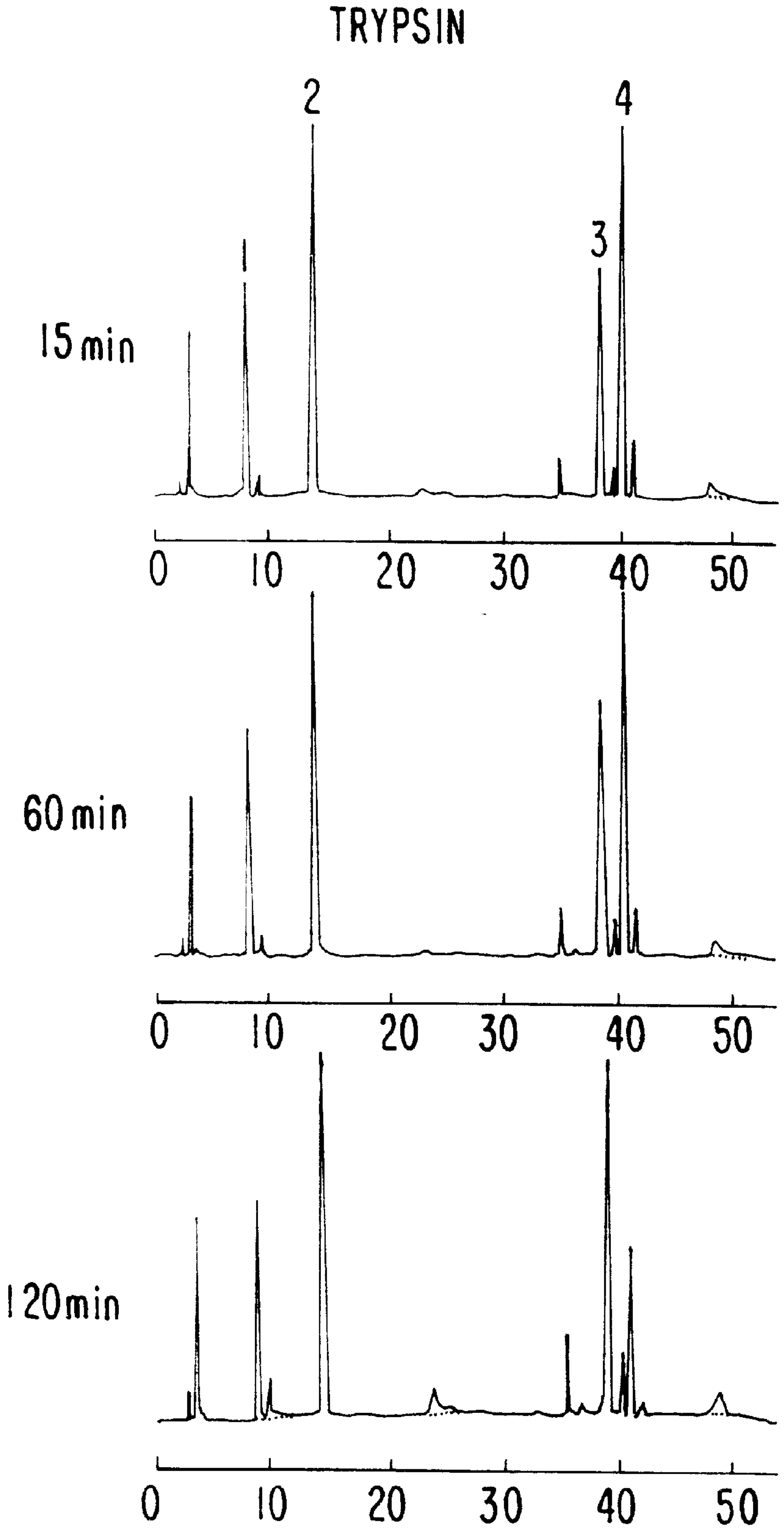
FIG. 4 shows the chromatograms obtained when glucagon is subjected to the action of trypsin (as obtained after 15, 60 and 120 minutes of incubation, respectively)
Figure 5:
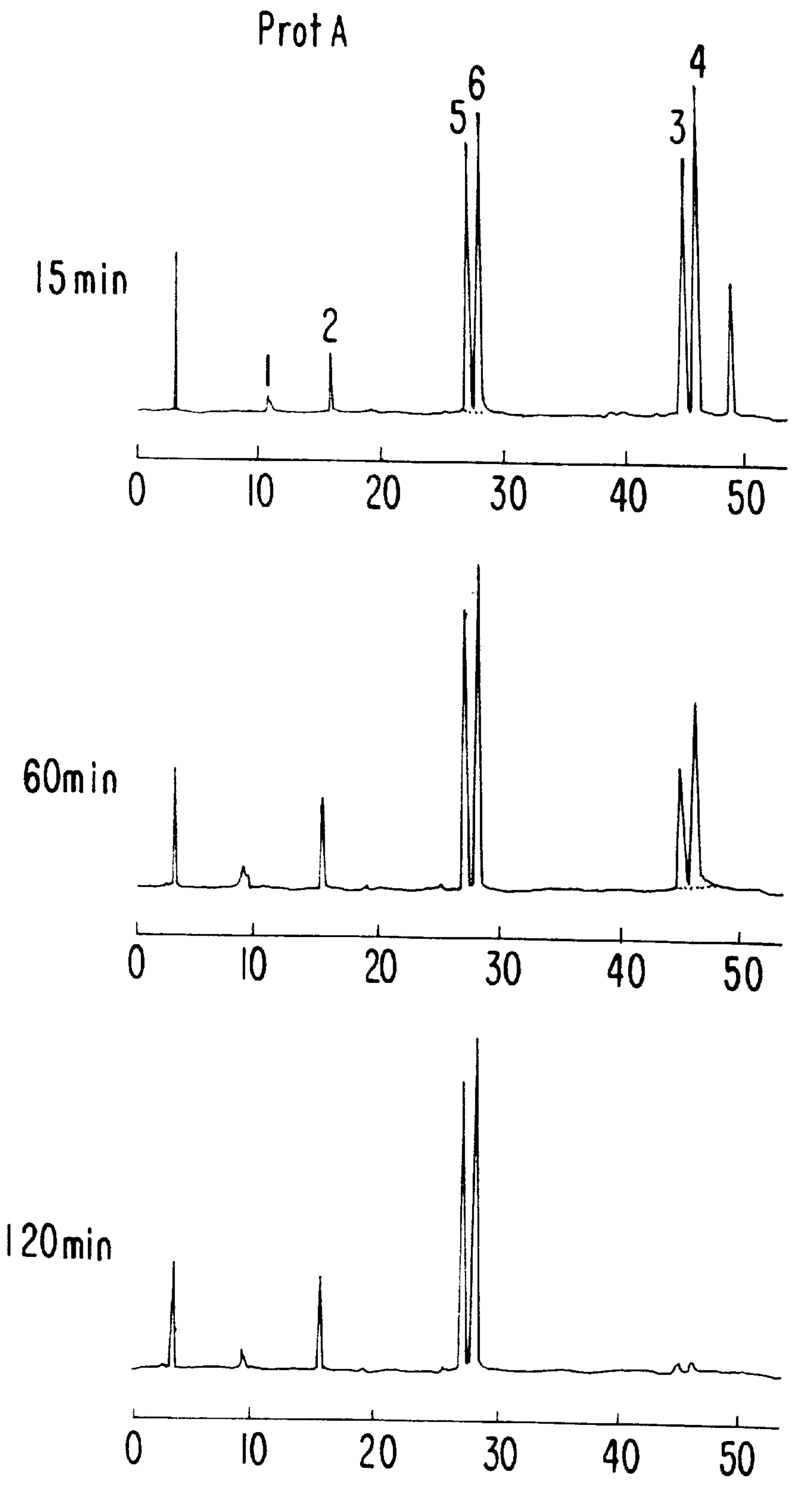
FIG. 5 shows the chromatograms obtained when glucagon is subjected to the action of an enzyme of the invention (ProtA) (as obtained after 15, 60 and 120 minutes of incubation, respectively).

The results of the hydrolysis of glucagon are presented in FIGS. 4 and 5. From the chromatograms obtained with trypsin (FIG. 4) it appears that the Arg—Arg and the Lys-Tyr bonds are equally accessible. The decrease in peak 4 and increase in peak 3 is caused by a second activity towards the Arg-Ala bond.

From the chromatograms obtained with the proteolytic enzyme of the invention (ProtA, FIG. 5) it appears that it has a preference for the Arg—Arg and the Trp-Leu bond (peak 5 and 6), which is in contrast to trypsin. A weaker secondary activity towards the Lys-Tyr bond is indicated by peak 2.

We claim:

1. A proteolytic enzyme derived from a strain of Amycolata or a strain of Amycolatopsis.

2. The proteolytic enzyme of claim 1, which is derived from a strain of *Amycolata autotrophica*, a strain of *Amycolata hydrocarbonoxydans*, or a strain of *Amycolata saturnea.*

3. The proteolytic enzyme of claim 1, which is derived from a strain of *Amycolatopsis mediterranei*, a strain of *Amycolatopsis methanolica*, a strain of *Amycolatopsis fastidiosa*, a strain of *Amycolatopsis orientalis*, a strain of *Amycolatopsis rugosa*, or a strain of *Amycolatopsis sulphurea.*

4. The proteolytic enzyme of claim 1, which is derived from a strain of *Amycolatopsis mediterranei.*

5. The proteolytic enzyme of claim 4, which is derived from the strain *Amycolatopsis mediterranei* ATCC 13685, the strain *Amycolatopsis mediterranei* ATCC 21271, the strain *Amycolatopsis mediterranei* ATCC 21411, the strain *Amycolatopsis mediterranei* ATCC 21789, the strain *Amycolatopsis mediterranei* ATCC 27642, the strain *Amycolatopsis mediterranei* ATCC 31064, the strain *Amycolatopsis mediterranei* ATCC 31065, the strain *Amycolatopsis mediterranei* ATCC 31066, or a mutant thereof.

6. The proteolytic enzyme of claim 5, which is derived from the strain *Amycolatopsis mediterranei* ATCC 13685, or a mutant thereof.

7. The proteolytic enzyme of claim 1, which enzyme has activity towards lysine and/or arginine bonds.

8. The proteolytic enzyme of claim 1, which enzyme has more than 90% activity in the range of from about pH 8 to about pH 11, determined on casein substrate at 25° C.

9. The proteolytic enzyme of claim 1, which enzyme has a temperature optimum within the range of from 30 to 45° C., determined on casein substrate at pH 9.5.

10. The proteolytic enzyme of claim 1, which enzyme has a molecular weight of about 33 kDa as determined by SDS-PAGE.

11. The proteolytic enzyme of claim 1, which enzyme has an isoelectric point (pI) of about 9.1.

12. The proteolytic enzyme of claim 1, which enzyme has activity on the Z-Arg-pNA (ZAPA) substrate, but no activity on the Suc-Ala-Ala-Pro-Phe-pNA substrate.

13. A process for the preparation of the proteolytic enzyme of claim 1, which process comprises cultivation of a protease producing strain of Amycolata or a protease producing strain of Amycolatopsis in a suitable nutrient medium, containing carbon and nitrogen sources and other inorganic salts, followed by recovery of the proteolytic enzyme.

14. The process of claim 13, in which the protease producing strain is a strain of *Amycolatopsis mediterranei*, a strain of *Amycolatopsis methanolica*, a strain of *Amycolatopsis fastidiosa*, a strain of *Amycolatopsis orientalis*, a strain of *Amycolatopsis rugosa*, or a strain of *Amycolatopsis sulphurea.*

15. The process of claim 14, in which the protease producing strain is a strain of *Amycolatopsis mediterranei.*

16. The process of claim 15, in which the protease producing strain is the strain *Amycolatopsis mediterranei* ATCC 13685, the strain *Amycolatopsis mediterranei* ATCC 21271, the strain *Amycolatopsis mediterranei* ATCC 21411, the strain *Amycolatopsis mediterranei* ATCC 21789, the strain *Amycolatopsis mediterranei* ATCC 27642, the strain *Amycolatopsis mediterranei* ATCC 31064, the strain *Amycolatopsis mediterranei* ATCC 31065, the strain *Amycolatopsis mediterranei* ATCC 31066, or a mutant thereof.

17. The process of claim 13, in which the protease producing strain is a strain of *Amycolata autotrophica*, a strain of *Amycolata hydrocarbonoxydans*, or a strain of *Amycolata saturnea.*

18. A process for the preparation of the proteolytic enzyme of claim 1, which process comprises isolating a DNA fragment encoding the proteolytic enzyme; combining the DNA fragment with an appropriate expression signal in an appropriate plasmid vector; introducing the plasmid vector into an appropriate host either as an autonomously replicating plasmid or integrated into the chromosome; cultivating the host organism under conditions leading to expression of the proteolytic enzyme; and recovering of the proteolytic enzyme from the culture medium.

19. The process of claim 18, in which the host organism is a strain of *Escherichia coli*, a strain of Bacillus, a strain of Aspergillus, or a strain of Streptomyces.

20. A detergent composition comprising a proteolytic enzyme of claim 1.

21. The detergent composition of claim 20, which comprises one or more additional enzymes selected from the group consisting of an amylase, a lipase, a cutinase, a protease, a cellulase, a peroxidase, and an oxidase.

22. A detergent additive comprising a proteolytic enzyme of claim 1.

23. The detergent additive of claim 22, provided in the form of a non-dusting granulate, a stabilized liquid, or a protected enzyme.

* * * * *